United States Patent
Govari et al.

(10) Patent No.: US 11,246,505 B2
(45) Date of Patent: Feb. 15, 2022

(54) USING RADIOFREQUENCY (RF) TRANSMISSION SYSTEM TO FIND OPENING IN TISSUE WALL

(71) Applicant: BIOSENSE WEBSTER (ISRAEL) LTD., Yokneam (IL)

(72) Inventors: Assaf Govari, Haifa (IL); Andres Claudio Altmann, Haifa (IL); Vadim Gliner, Haifa (IL); Alon Boumendil, Givat Nili (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 625 days.

(21) Appl. No.: 16/177,977

(22) Filed: Nov. 1, 2018

(65) Prior Publication Data
US 2020/0138333 A1    May 7, 2020

(51) Int. Cl.
*A61B 5/06* (2006.01)
*A61B 5/367* (2021.01)
*A61B 5/107* (2006.01)
*A61B 5/00* (2006.01)

(52) U.S. Cl.
CPC ............ *A61B 5/063* (2013.01); *A61B 5/062* (2013.01); *A61B 5/1076* (2013.01); *A61B 5/367* (2021.01); *A61B 5/6859* (2013.01); *A61B 5/6886* (2013.01); *A61B 5/7425* (2013.01); *A61B 2562/0257* (2013.01)

(58) Field of Classification Search
CPC ......... A61B 5/367; A61B 5/061; A61B 5/063; A61B 5/065; A61B 5/068; A61B 5/0538; A61B 5/287; A61B 5/0536
See application file for complete search history.

(56) References Cited

U.S. PATENT DOCUMENTS

| | | | |
|---|---|---|---|
| 5,078,714 A * | 1/1992 | Katims | A61B 5/068 604/264 |
| 5,391,199 A | 2/1995 | Ben-Haim | |
| 5,846,196 A | 12/1998 | Siekmeyer et al. | |
| 6,239,724 B1 | 5/2001 | Doron et al. | |
| 6,332,089 B1 | 12/2001 | Acker et al. | |

(Continued)

FOREIGN PATENT DOCUMENTS

| | | |
|---|---|---|
| EP | 3254613 A2 | 12/2017 |
| WO | WO 96/05768 A1 | 2/1996 |

OTHER PUBLICATIONS

Pending U.S. Appl. No. 15/991,291, filed May 29, 2018.

(Continued)

*Primary Examiner* — Carolyn A Pehlke
*Assistant Examiner* — Johnathan Maynard

(57) ABSTRACT

A method includes receiving, from a probe that includes electrodes and is positioned inside a cavity in an organ of a patient, (i) proximity signals indicative of proximity of the electrodes to a wall of the cavity, and (ii) position signals indicative of positions of the electrodes within the cavity. Based on the proximity signals and the position signals, at least a portion of a volume of the cavity is represented by a sphere model including multiple spheres. A direction is identified along which one or more spheres are larger than one or more surrounding spheres by at least a given factor. Based on the indicated direction, a location of an opening in the wall of the cavity is estimated and presented to a user.

8 Claims, 3 Drawing Sheets

(56) References Cited

U.S. PATENT DOCUMENTS

| | | |
|---|---|---|
| 6,484,118 B1 | 11/2002 | Govari |
| 6,618,612 B1 | 9/2003 | Acker et al. |
| 6,690,963 B2 | 2/2004 | Ben-Haim et al. |
| 6,773,402 B2 | 8/2004 | Govari |
| 7,610,078 B2 | 10/2009 | Willis |
| 7,756,576 B2 | 7/2010 | Levin |
| 7,848,787 B2 | 12/2010 | Osadchy |
| 7,869,865 B2 | 1/2011 | Govari et al. |
| 8,456,182 B2 | 6/2013 | Bar-Tal et al. |
| 2001/0009976 A1 | 7/2001 | Panescu et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2004/0242984 A1 | 12/2004 | Plaza |
| 2004/0243018 A1* | 12/2004 | Organ ................ A61B 5/0531 600/547 |
| 2005/0107718 A1 | 5/2005 | Hashimshony |
| 2006/0116576 A1 | 6/2006 | McGee et al. |
| 2006/0287649 A1 | 12/2006 | Ormsby et al. |
| 2007/0032747 A1 | 2/2007 | Hashimshony et al. |
| 2007/0185485 A1* | 8/2007 | Hauck ................ A61B 34/20 606/41 |
| 2009/0306643 A1* | 12/2009 | Pappone ............. A61B 34/20 606/33 |
| 2010/0179632 A1* | 7/2010 | Bruszewski ....... A61B 18/1492 623/1.11 |
| 2012/0158011 A1 | 6/2012 | Sandhu et al. |
| 2013/0072774 A1 | 3/2013 | Greenspan |
| 2018/0078170 A1* | 3/2018 | Panescu ............ A61B 34/20 |
| 2021/0128009 A1* | 5/2021 | Ben-Haim .......... A61B 5/0538 |

OTHER PUBLICATIONS

Pending U.S. Appl. No. 16/141,125, filed Sep. 25, 2018.
European Search Report for corresponding EPA No. 19206567.0 dated Jan. 10, 2020.

* cited by examiner

USING RADIOFREQUENCY (RF) TRANSMISSION SYSTEM TO FIND OPENING IN TISSUE WALL

FIELD OF THE INVENTION

The present invention relates generally to intra-body probes, and particularly to cardiac electroanatomical mapping using a catheter.

BACKGROUND OF THE INVENTION

Various techniques were proposed for anatomical mapping of a cavity wall tissue. For example, U.S. Patent Application Publication 2005/0107718 describes a method and system for examining tissue in order to differentiate it from other tissue according to the dielectric properties of the examined tissue, by: applying a probe to the tissue to be examined, such that the probe generates an electrical fringe field in the zone of the examined tissue and produces a reflected pulse therefrom with negligible radiation penetrating into the tissue itself; detecting the reflected electrical pulse; and comparing electrical characteristics of the reflected electrical pulse with respect to the applied electrical pulse to provide an indication of the dielectric properties of the examined tissue.

As another example, U.S. Patent Application Publication 2007/0032747 describes a device for tissue-characterization, designed for effective sensor-to-tissue contact. The device includes an element, having a rigid surface of a linear cross-section, on which at least one sensor is arranged, and a mechanism for applying a force to a soft tissue, the line of force being at an acute angle with the rigid surface, for stretching or stretching and pushing the soft tissue against the rigid surface, thus achieving effective contact between the tissue and the at least one sensor. In consequence, the accuracy of the sensing is improved. In accordance with another embodiment, a plurality of sensors is employed, arranged along a curved element, for providing three-dimensional information regarding the tissue, for example, by small-scale computerized tomography.

U.S. Patent Application Publication 2006/0116576 describes systems and a method for navigating a catheter relative to a heart. A mark, such as a point or line, representing an anatomical region of interest, such as cardiac tissue targeted for treatment, is displayed on a representation of the anatomical body. The positions of the medical probe and the mark are determined within a three-dimensional coordinate system, and the proximity between the medical probe and the mark determined based on these positions. This proximity can then be indicated to a user, e.g., using graphics, text, or audible sounds.

SUMMARY OF THE INVENTION

An embodiment of the present invention provides a method including receiving, from a probe that includes electrodes and is positioned inside a cavity in an organ of a patient, (i) proximity signals indicative of proximity of the electrodes to a wall of the cavity, and (ii) position signals indicative of positions of the electrodes within the cavity. Based on the proximity signals and the position signals, at least a portion of a volume of the cavity is represented by a sphere model including multiple spheres. A direction is identified along which one or more spheres are larger than one or more surrounding spheres by at least a given factor. Based on the indicated direction, a location of an opening in the wall of the cavity is estimated and presented to a user.

In some embodiments, identifying the direction includes constructing, based on the sphere model, a surface corresponding to the wall, and identifying that radii of one or more spheres along the surface are larger than the radii of neighboring spheres by at least the given factor.

In some embodiments, the method further includes storing the estimated location of the opening in a memory.

In an embodiment, presenting the location includes displaying the location of the opening to the user, overlaid on an anatomical map of the portion of the wall.

There is additionally provided, in accordance with an embodiment of the present invention, a system including an interface and a processor. The interface is configured to receive, from a probe that includes electrodes and is positioned inside a cavity in an organ of a patient, (i) proximity signals indicative of proximity of the electrodes to a wall of the cavity, and (ii) position signals indicative of positions of the electrodes within the cavity. The processor is configured to, based on the proximity signals and the position signals, represent at least a portion of a volume of the cavity by a sphere model including multiple spheres, and to identify a direction along which one or more spheres are larger than one or more surrounding spheres by at least a given factor, the processor is further configured to, based on the indicated direction, estimate a location of an opening in the wall of the cavity, and present the location of the opening to a user.

The present invention will be more fully understood from the following detailed description of the embodiments thereof, taken together with the drawings in which:

DETAILED DESCRIPTION OF EMBODIMENTS

Overview

Figure 1:
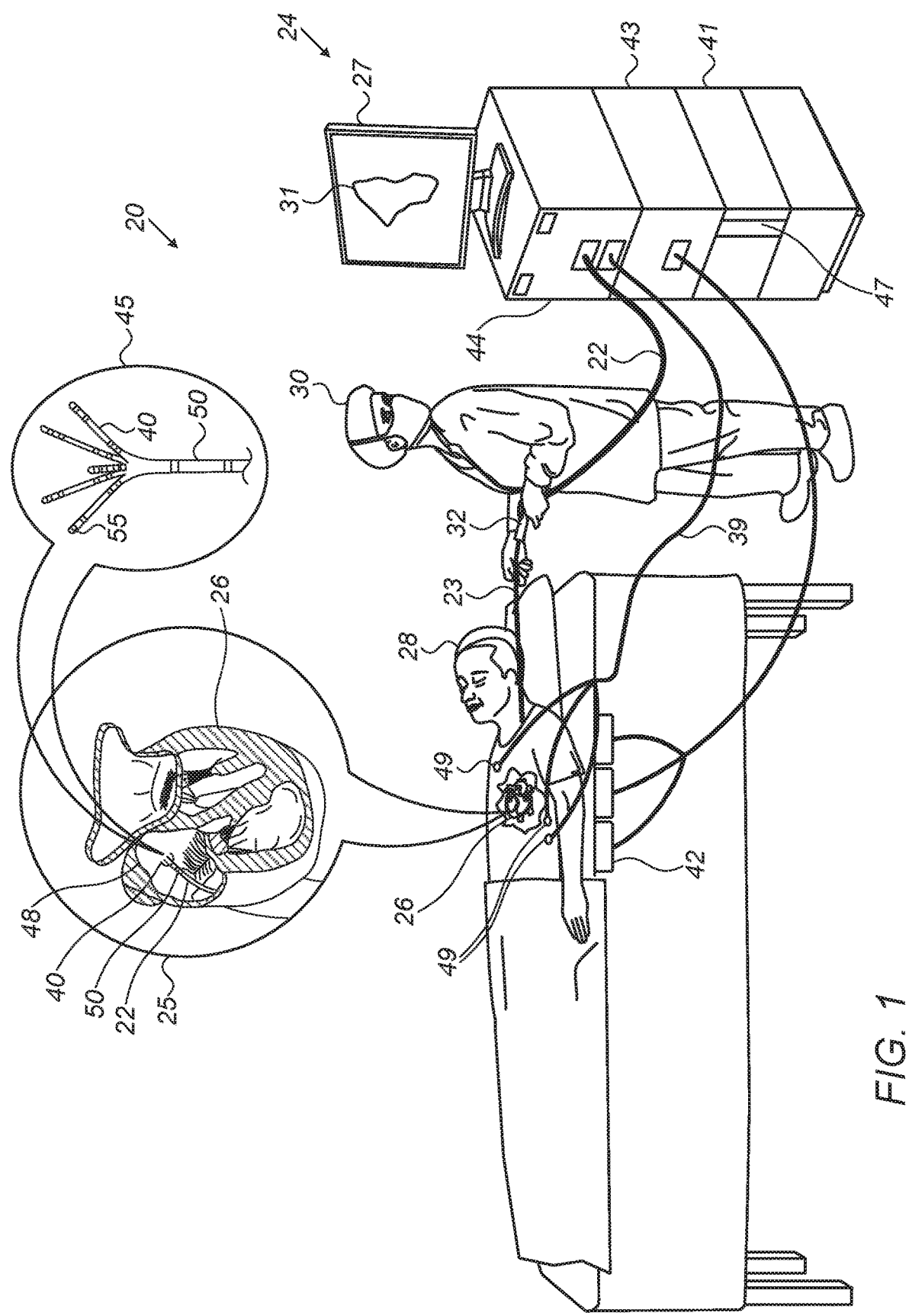
FIG. 1 is a schematic, pictorial illustration of a system for electro-anatomical mapping, in accordance with an embodiment of the present invention.

One of the applications of catheter-based anatomical mapping of a cavity of an organ is to find one or more locations where an opening exists in the cavity's wall tissue. For example, mapping the left atrium of a heart may involve finding the openings of the four pulmonary veins. In some cases, however, a mapping technique may not find an anatomical opening in the volume, due to, for example, a difficulty of the catheter to follow the anatomy near an opening. A resulting low-resolution map may require a trained, qualified person, such as a radiologist or a cardiologist, to identify an opening. In some cases, however, even a professional may require a time-consuming trial and error approach to find an opening during a catheterization procedure.

To ease finding an opening in a tissue wall of a cavity, embodiments of the present invention that are described hereinafter provide a radiofrequency (RF) transmission system and method for finding opening, which do not require the catheter to closely follow the anatomy in the vicinity of an opening. The disclosed method relies on tissue typically having a higher impedance than blood, especially in the low RF frequency range of 1-4 KHz. Thus, measured values of impedances would typically increase as the catheter nears a cavity wall.

In some embodiments, during an electro-anatomical mapping session, the disclosed system conducts impedance measurements using a catheter with multiple distal-electrodes positioned in the cavity. The measured impedances are typically bi-polar impedances (impedances between pairs of distal-electrodes) in one or more RF frequency ranges. A processor uses the measured impedances, along with a prior calibration process, to estimate a location of an opening in the cavity wall.

A radiofrequency (RF) transmission system that can be used for this purpose is described, for example, in a U.S. patent application Ser. No. 16/141,125, filed Sep. 25, 2018, entitled "RF Transmission System To Find Tissue Proximity," which is assigned to the assignee of the present patent application and whose disclosure is incorporated herein by reference.

In some embodiments, the mapping involves three stages:

Data Acquisition Stage

In some embodiments, while the catheter moves across the cardiac chamber, a position-tracking system measures various positions P of the catheter distal end. The system uses, for example, a magnetic sensor that is fitted at the distal end of the catheter. The sensor outputs, in response to externally-applied magnetic fields, position signals which are received by a processor of the position-tracking system. Based on the position signals, the processor derives catheter positions P inside the cardiac chamber.

In parallel, i.e., while the catheter moves across the cavity, a position-tracking system measures respective positions P of the catheter distal end inside the cavity, using, for example, a magnetic sensor that is fitted at the distal end of the catheter. The sensor acquires position signals which are received by a processor, such as a processor of the position-tracking system from which the processor derives positions P.

In some embodiments, based on measured positions P, and based on the respective impedances (which are indicative of a wall tissue proximity to the catheter, acquired at the respective positions P), a processor constructs a cavity sphere model. The sphere model represents at least a portion of the cavity volume by a set of partially overlapping spheres $\{(P, \rho)\}$. Each sphere is described by (a) a known location, P, of its center, and, (b) an unscaled radius, $\rho$, which is indicative of a relative distance between location P and the cavity wall.

In an embodiment, (i) the magnetically measured positions P are the centers P of the spheres $\{(P, \rho)\}$, and (ii) the unscaled radii $\rho$ are derived from the electrical impedances, such that, as an impedance becomes higher, $\rho$ becomes smaller. Therefore, in the disclosed cavity representation, spheres $(P, \rho)$ which have centers P further away from a cavity wall are larger than spheres located closer to a cavity wall. The transition from larger to smaller diameter spheres is typically gradual and "smooth."

Calibration Stage

To scale radiuses $\rho$ into absolute values R, (i.e., to calibrate $\rho$), the processor uses instances when the distal end comes into physical contact with cavity wall tissue. When an electrode pair comes in physical contact with a location over cavity wall tissue, the processor correlates the bi-polar signals with a geometrically known distance between the electrode-pair and the magnetic sensor, which is at a respective location, yielding a reference sphere (P, R) for scaling the radiuses of set of spheres $\{(P, \rho)\}$. In some embodiments, the processor scales the radiuses of the sphere model in a certain portion of the cavity based on a location in which the catheter is known to have made physical contact with the cavity wall (tissue). To detect physical contact at the location, the system may employ the distal electrodes and/or a dedicated sensor, such as a contact-force sensor, or other methods and means known in the art.

Opening Finding Stage

Once calibration has been conducted, if the catheter is close to an opening in the wall tissue, the processor typically identifies one or more spheres in the direction of the wall tissue having diameters anomalously larger (e.g., with a ratio of sizes above a given ratio) than the diameters of at least part of the surrounding spheres, which is indicative of an opening. Correspondingly, the processor indicates to a user where an opening in the wall might be located.

In some embodiments, the processor estimates the location of an opening in the cavity wall by finding a direction toward which the opening exists, for example, relative to a measured position. To indicate the direction, the processor constructs a surface corresponding to the wall, wherein the radii of one or more spheres along that surface are larger than the radii of neighboring spheres by at least a given factor. The indicated direction is perpendicular to the surface where the direction points to the possible opening.

The disclosed system and method can be applied with various types of catheters to provide local information, such as a distance between an electrode of a catheter and wall tissue and/or to rapidly acquire global information, such as a map that may include the entire cavity, e.g., an entire cardiac cavity.

The disclosed RF transmission system minimally perturbs cardiac tissue physically and electrically as (a) the RF technique does not require a physician to advance the catheter against tissue to tightly follow anatomy, and (b) the RF technique applies low-voltage bi-polar signals having high-frequency (i.e., far above any bio-physiological activation frequency).

Typically, the Processor is programmed in software containing a particular algorithm that enables the processor to conduct each of the processor related steps and functions outlined above.

The disclosed RF transmission system for finding an opening in a wall tissue of a cavity gives a physician an efficient and safe means for obtaining clinical information to support treatment decisions, such as where to ablate cardiac tissue so as to inhibit an arrhythmia. The disclosed technique may thus simplify and expedite complicated minimally invasive procedures, such as those required in cardiac catheterizations.

SYSTEM DESCRIPTION

FIG. 1 is a schematic, pictorial illustration of an electro-anatomical mapping system 20, in accordance with an embodiment of the present invention. As seen, a physician 30 navigates a PENTARAY® catheter 40 (made by Biosense-Webster, Irvine, Calif.), seen in detail in inset 45, to a target location in a heart 26 of a patient 28 by manipulating shaft 22 using a manipulator 32 near the proximal end of the catheter and/or deflection from a sheath 23.

Catheter 40 is inserted, in a folded configuration, through sheath 23, and only after sheath 23 is retracted does catheter 40 regain its intended functional shape. By containing catheter 40 in a folded configuration, sheath 23 also serves to minimize vascular trauma on its way to the target location.

FIG. 1 depicts a physician 30 using catheter 40, seen in inset 25, performing an electro-anatomical mapping of a cavity of heart 26, having a cavity wall 48, of a patient 28. In some embodiments, system 20 determines the position and/or the proximity of cardiac wall 48 to catheter 40 tissue a cavity of heart 26, as described below.

Catheter 40 incorporates a magnetic sensor 50 on a shaft 22. Catheter 40 further comprises one or more arms, which may be mechanically flexible, to each of which are coupled one or more distal-electrodes 55, as seen in inset 45. Magnetic sensor 50 and distal-electrodes 55 are connected by wires running through shaft 22 to various driver circuitries in a console 24.

In some embodiments, system 20 comprises a magnetic-sensing sub-system to estimate the position of catheter 40 inside a cardiac chamber of heart 26. Patient 28 is placed in a magnetic field generated by a pad containing magnetic field generator coils 42, which are driven by unit 43. The magnetic fields generated by coils 42 generate position signals in a magnetic sensor 50, which are then provided as corresponding electrical inputs to a processor 41, which uses them to calculate the position of catheter 40.

The method of position sensing using external magnetic fields and sensor 50 is implemented in various medical applications, for example, in the CARTO™ system, produced by Biosense Webster, and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Processor 41, typically a general-purpose computer, is further connected via suitable front end and interface circuits 44, to receive signals from surface-electrodes 49. Processor 41 is connected to surface-electrodes 49 by wires running through a cable 39 to the chest of patient 28. In some embodiments, processor 41 estimates the position of catheter 40 inside a cavity by correlating electrical position signals received from either distal-electrodes 55 and/or surface-electrodes 49 with position-calibrated electrical signals acquired previously. The method of electrode position sensing using calibrated electrical signals is implemented in various medical applications, for example in the CARTO™ system, produced by Biosense-Webster, and is described in detail in U.S. Pat. Nos. 7,756,576, 7,869,865, 7,848,787, and 8,456,182, whose disclosures are all incorporated herein by reference.

In some embodiments, during a mapping procedure, distal-electrodes 55 acquire and/or inject radiofrequency (RF) bi-polar signals (i.e., differential electrical signals between pairs of distal-electrodes 55). Signals traveling at least partially through the tissue of wall 48 are typically more attenuated than these traveling through the blood of heart 26. A processor 41 receives the various RF bi-polar proximity signals via an electrical interface 44, and uses bio-impedance information contained in these signals to construct an electro-anatomical map 31 of the cavity, as further elaborated below. During and/or following the procedure, processor 41 may display electro-anatomical proximity map 31 on a display 27.

In some embodiments, processor 41 is further configured to estimate and verify the quality of physical contact between each of distal-electrodes 55 and wall 48 surface of the cardiac cavity during measurement, so as to correlate the RF bi-polar proximity indicative signals with known distances. Using the correlated bi-polar proximity signals, and the respective positions measured by sensor 50, processor 41 constructs a cavity sphere model, which is used to identify, for example, an opening in wall 48.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

In particular, processor 41 runs a dedicated algorithm that enables processor 41 to perform the disclosed steps, comprising calculations of proximities and positions, calibrations, and calculating the cavity surface, as further described below.

The example illustration shown in FIG. 1 is chosen purely for the sake of conceptual clarity. FIG. 1 shows only elements related to the disclosed techniques, for the sake of simplicity and clarity. System 20 typically comprises additional modules and elements that are not directly related to the disclosed techniques, and thus are intentionally omitted from FIG. 1 and from the corresponding description. The elements of system 20 and the methods described herein may be further applied, for example, to control an ablation of wall 48 tissue of heart 26 using part of distal-electrodes 55.

Other types of sensing and/or therapeutic catheters, such as DECANAV®, SMARTTOUCH®, and LASSO® Catheter (all produced by Biosense-Webster) may equivalently be employed.

Using RF Transmission System to Find Opening in Tissue Wall

Figure 2:
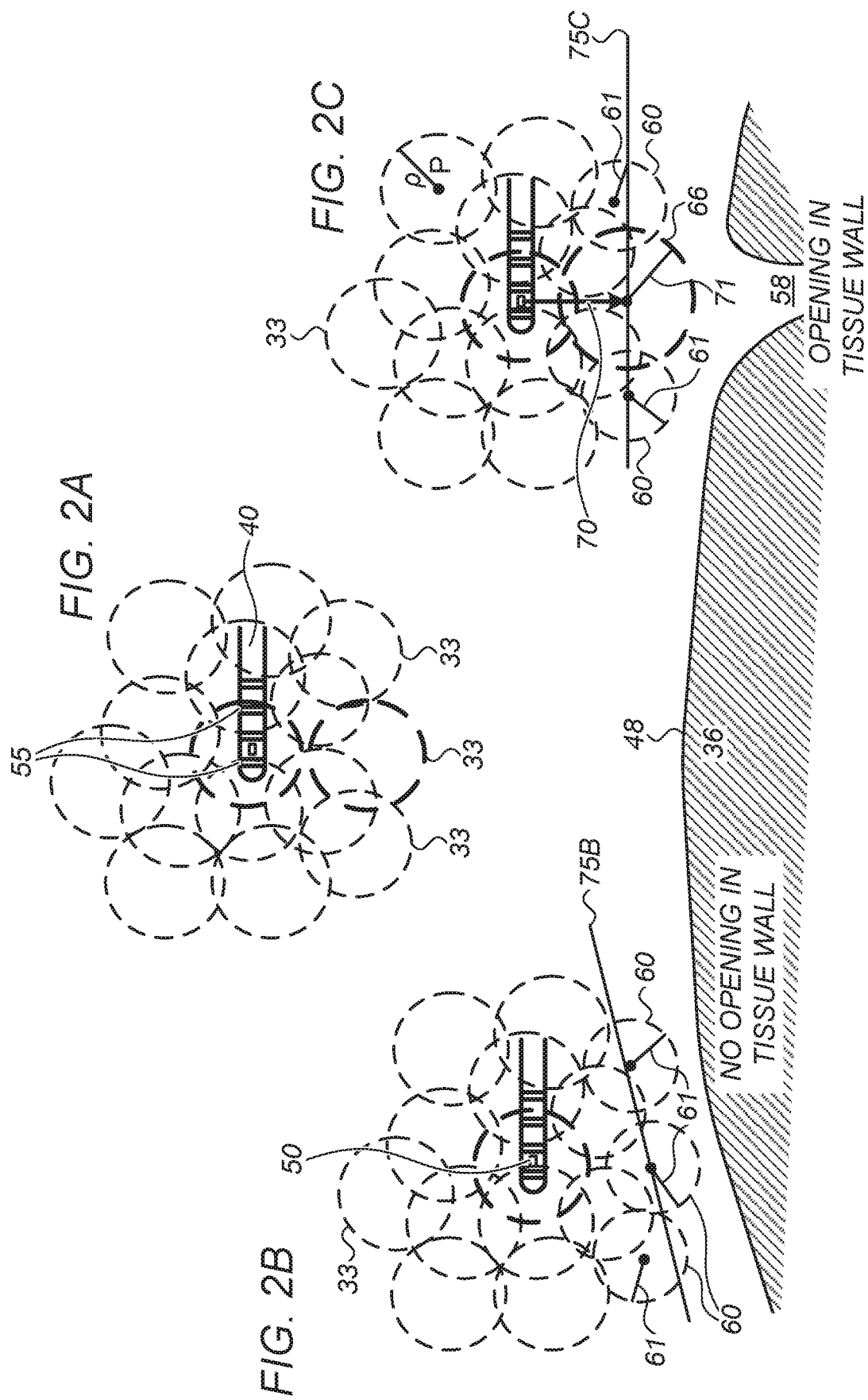
FIGS. 2A-2C are schematic side-views of a derived cavity-sphere model in close and distant proximity to an opening in a cavity wall tissue, in accordance with embodiments of the present invention.

FIGS. 2A-2C are schematic side-views of a cavity-sphere model in both close and distant proximity to an opening in a cavity wall tissue, in accordance with embodiments of the present invention. In FIGS. 2A-2C, the distal end of catheter 40 is seen immersed in the cavity blood, in variable vicinities of tissue 36 of the cavity wall 48.

FIG. 2A shows a focal catheter, such as the DECANAV® catheter, which comprises multiple distal-electrodes 55. In an embodiment, distal-electrodes 55 are used to inject, and receive, bi-polar currents (shown schematically as curved arrows 60) at different RF frequency ranges. As seen, some of the electrical paths pass partly in tissue, whereas others pass entirely in blood.

In an embodiment, the process is preset, in the sense that injection and receiving electrodes are selected in advance, as are the frequencies and driving voltages of the currents provided to the injection electrodes.

In some embodiments, the different electrical frequency ranges comprise the ranges of 1-4 kHz and 12-100 kHz. The reason for using two different frequency ranges is that impedance at the 12-100 kHz range is practically insensitive to tissue 36, whereas signals at the 1-4 kHz range show measurable sensitivity to tissue 36. Using the high frequency as reference, small changes in the low-frequency impedances, i.e., as a function of proximity of tissue, can be accurately resolved.

Data Acquisition Stage

In an embodiment, as catheter 40 moves within the cardiac cavity, processor 41 receives impedance measurements measured between pairs of distal-electrodes 55. Each impedance measurement depends on the transmitting and receiving electrodes, the injection frequencies and voltages, as well as the intervening material (blood and/or tissue).

Typically, tissue has a higher impedance than blood, especially in the lower frequency range, so that impedances are generally higher if the electrodes are in close proximity to wall 48 of tissue 36, and vice versa. The dependence of impedances on frequency and on blood and/or tissue, in an embodiment, is provided in U.S. patent application Ser. No. 15/991,291, filed May 29, 2018, cited above.

In FIG. 2A catheter 40 is positioned closer to the center of the cavity, approximately equidistant from the cavity walls, as processor 40 correspondingly constructs spheres 33 of the cavity sphere model that have approximately equal diameters at all directions.

Processor 41 correlates each impedance measured with electrode pair 55 with a respective position measured by position sensor 50 at which the bi-polar impedances are measured, as described in U.S. patent application Ser. No. 16/141,125, filed Sep. 25, 2018, cited above.

Calibration Stage

At instances in which catheter 40 comes into contact with the cavity wall 48, processor 41 correlates the bi-polar signals with a geometrically known distance between the electrode-pair and the magnetic sensor, which is at a respective location. The occurrence of physical contact may be determined by any suitable sensor, for example by a force measured by a force sensor in catheter 40, and/or a change of impedance between selected distal-electrodes 55.

Opening Finding Stage

In an embodiment, as catheter 40 moves across the cavity closer to cavity wall 48, the cavity sphere model reflects this proximity. As seen in FIG. 2B, spheres 60 in the direction of wall 48 are smaller than spheres 33. Based on that property of the sphere model, processor 41 generates a local anatomical shape of wall 48, which is shown in FIG. 2B, by way of example, as a linear contour 75B.

Since all spheres 60 along contour 75B (contour 57B locally representing wall 48) are all approximately the same size, i.e., approximately the same radius 61, the resulting anatomical map shape is rather uniform, reflecting a substantially unchanging cavity wall.

When, on the other hand, catheter 40 is moved closer to an opening 58 in cavity wall 48, as seen in FIG. 3C, the cavity sphere model includes one or more anomalously sized spheres in the direction of wall 48. As seen, sphere 66, in the direction of the opening, is anomalously larger than neighboring spheres 60 that are located along a contour 75C, by a at least a given factor. In other words, the ratio of radius 71 to radii 61 of neighboring spheres is above a given minimum. As seen, an arrow 70 designates the direction derived by processor 41, along which the processor estimates opening 58 to be located over cavity wall 48. In FIG. 2C, linear contour 75C represents, by way of example, a surface that is locally perpendicular to arrow 70.

The illustrations in FIGS. 2A-2C are brought purely for the sake of conceptual clarity. For example, some of the shown spheres may not be to exact scale, for clarity of presentation. In an embodiment, a given ratio of radii between sphere 66 and sphere 60 is used as a minimum criterion over which processor 41 estimates that an opening 58 exists in cavity wall 48 (i.e., a given ratio of radii between neighboring spheres 66 and 60 is above a given minimum).

Figure 3:
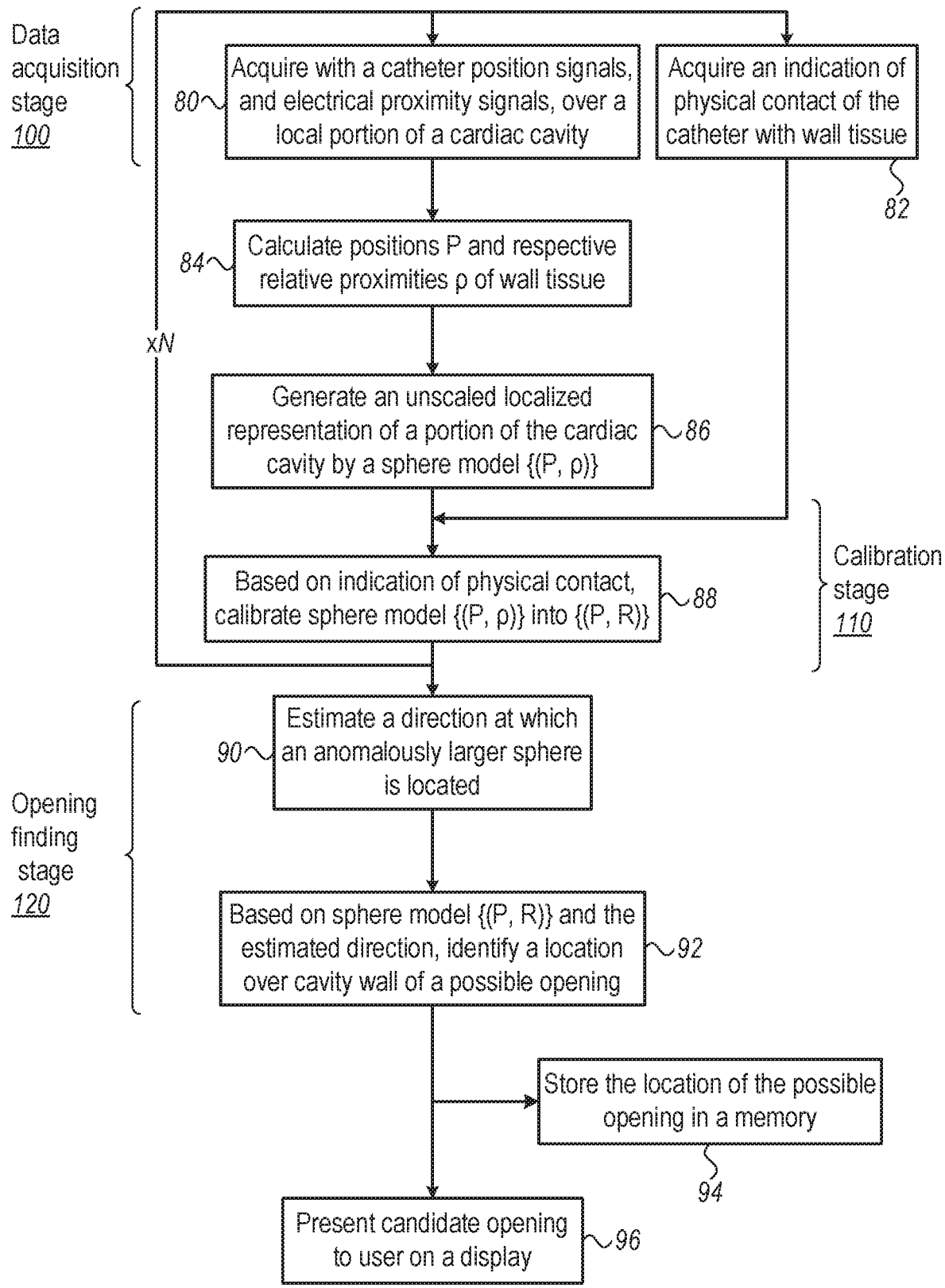
FIG. 3 is a flow chart that schematically illustrates a method for identifying an opening in a cavity wall, in accordance with an embodiment of the present invention.

FIG. 3 is a flow chart that schematically illustrates a method for identifying an opening in a cavity wall, in accordance with an embodiment of the present invention. Typically, processor 41 is programmed with software that carries out the various steps of this algorithm.

Data Acquisition Stage 100 (Steps 80-82)

The process begins with physician 30 moving catheter 40, which is equipped with magnetic sensor 50, inside a cardiac cavity to acquire multiple magnetic position signals and bi-polar electrical proximity signals, at a proximity data acquisition step 80.

In parallel, catheter 40, which comprises means to detect physical contact with the cardiac cavity wall, occasionally indicates to processor 41 of a physical contact that catheters 40 make with wall tissue, at an acquire physical contact indication step 82.

Based on the position signals and respective proximity signals, and using the dedicated algorithm, processor 41 calculates positions and respective relative (i.e., unscaled) proximities, at a position and unscaled proximity calculation step 84. Next, processor 41 represents a portion of the cardiac cavity with spheres $\{(P, \rho)\}$, at a local sphere-model construction step 86.

Calibration Stage 110

Next, based on indication of physical contact in the vicinity, i.e., at step 82, processor 41 calibrates the sphere-model into a model of spheres of known radius, $\{(P, R)\}$, at a calibration step 88. Steps 80-88 are typically repeated N times until a sufficient portion of the cavity wall is mapped.

Opening Finding Stage 120

Processor 41 analyzes the model to determine that there is an opening in cavity wall 48 in the vicinity of catheter 40, based, for example, on identifying that one or more spheres in a direction a cavity wall have anomalously larger radii $\rho$ compared with neighboring spheres, in an opening identification step 90.

Next, at an opening location estimation step 92, based on the sphere-model and the estimated direction in step 90, processor 41 estimates a location of the opening (e.g., opening) in the cavity's wall tissue. Processor 41 stores the location of the possible opening in memory 47, at a storing step 94. Finally, at a displaying step 96, processor 41 presents the found candidate opening to a user, on display 27. In an embodiment, the processor presents the location by displaying the location of the opening to the user, overlaid on an anatomical map of the portion of the wall The flow chart illustrated in FIG. 3 is highly simplified, for the sake of clarity. For example, in an embodiment, an analysis in step 84 may compare sizes of spheres to ones expected based on a known anatomy from a typical opening at the cavity wall, so as to increase the reliability of the finding.

Although the embodiments described herein mainly address cardiac applications, the methods and systems described herein can also be used in other applications, such as in renal applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:

receiving, from a probe that comprises electrodes and is positioned inside a cavity in an organ of a patient, (i) proximity signals indicative of proximity of the electrodes to a wall of the cavity, and (ii) position signals indicative of positions of the electrodes within the cavity;

based on the proximity signals and the position signals, representing at least a portion of a volume of the cavity by a sphere model comprising multiple spheres having a position and an unscaled radius;

calibrating the unscaled radius of the spheres to absolute values of radius by determining physical contact with cavity wall tissue;

Identifying a direction along which one or more spheres are larger than one or more surrounding spheres by at least a given factor;

based on the indicated direction, estimating a location of an opening in the wall of the cavity; and presenting the location of the opening to a user.

2. The method according to claim 1, wherein identifying the direction comprises constructing, based on the sphere model, a surface corresponding to the wall, and identifying that radii of one or more spheres along the surface are larger than the radii of neighboring spheres by at least the given factor.

3. The method according to claim 1, and comprising storing the estimated location of the opening in a memory.

4. The method according to claim 1, wherein presenting the location comprises displaying the location of the opening to the user, overlaid on an anatomical map of the portion of the wall.

5. A system, comprising:

an interface, configured to receive, from a probe that comprises electrodes and is positioned inside a cavity in an organ of a patient, (i) proximity signals indicative of proximity of the electrodes to a wall of the cavity, and (ii) position signals indicative of positions of the electrodes within the cavity; and a processor, configured to:

based on the proximity signals and the position signals, represent at least a portion of a volume of the cavity by a sphere model comprising multiple spheres having a position and an unscaled radius;

calibrate the unscaled radius of the spheres to absolute values of radius by determining physical contact with cavity wall tissue;

identify a direction along which one or more spheres are larger than one or more surrounding spheres by at least a given factor;

based on the indicated direction, estimate a location of an opening in the wall of the cavity; and present the location of the opening to a user.

6. The system according to claim 5, wherein the processor is configured to construct, based on the sphere model, a surface corresponding to the wall, and to identify the direction by identifying that radii of one or more spheres along the surface are larger than the radii of neighboring spheres by at least the given factor.

7. The system according to claim 5, wherein the processor is further configured to store the estimated location of the opening in a memory.

8. The system according to claim 5, wherein the processor is configured to present the location by displaying the location of the opening to the user, overlaid on an anatomical map of the portion of the wall.

* * * * *